(12) United States Patent
Lu et al.

(10) Patent No.: US 9,333,349 B2
(45) Date of Patent: May 10, 2016

(54) BIO-FEEDBACK TYPE DEVICE FOR PHYSICAL PAIN RELIEF AT CHILDBIRTH

(71) Applicant: Guangzhou Sunray Medical Apparatus Co., Ltd., Guangzhou (CN)

(72) Inventors: Yaosheng Lu, Guangzhou (CN); Jianguo Qi, Guangzhou (CN); Kun Fang, Guangzhou (CN); Ruyi Qin, Guangzhou (CN); Zhan Lin, Guangzhou (CN); Jingbo Rong, Guangzhou (JP); Haifeng Chen, Guangzhou (CN)

(73) Assignee: Guangzhou Sunray Medical Apparatus Co., Ltd., Guangzhou (CN)

( * ) Notice: Subject to any disclaimer, the term of this patent is extended or adjusted under 35 U.S.C. 154(b) by 0 days.

(21) Appl. No.: 14/646,956

(22) PCT Filed: Nov. 13, 2013

(86) PCT No.: PCT/CN2013/087035
§ 371 (c)(1),
(2) Date: May 22, 2015

(87) PCT Pub. No.: WO2014/079333
PCT Pub. Date: May 30, 2014

(65) Prior Publication Data
US 2015/0335886 A1      Nov. 26, 2015

(30) Foreign Application Priority Data

Nov. 26, 2012 (CN) .......................... 2012 1 0488575

(51) Int. Cl.
*A61N 1/00* (2006.01)
*A61N 1/36* (2006.01)
*A61B 5/00* (2006.01)

(52) U.S. Cl.
CPC .......... *A61N 1/36021* (2013.01); *A61B 5/4356* (2013.01); *A61B 5/486* (2013.01); *A61B 5/4824* (2013.01); *A61N 1/36014* (2013.01)

(58) Field of Classification Search
CPC .... A61B 5/4356; A61B 5/4824; A61B 5/486; A61N 1/36014; A61N 1/36021
See application file for complete search history.

(56) References Cited

U.S. PATENT DOCUMENTS

| 5,873,900 A | 2/1999 | Maurer et al. |
| 7,942,818 B2 | 5/2011 | Euliano et al. |

(Continued)

FOREIGN PATENT DOCUMENTS

| CN | 2216389 | 1/1996 |
| CN | 1148989 | 5/1997 |

(Continued)

OTHER PUBLICATIONS

International Searching Authority, Written Opinion of the International Searching Authority, PCT/CN2013/087035, Feb. 20, 2014.

(Continued)

*Primary Examiner* — George Manuel
(74) *Attorney, Agent, or Firm* — Greer, Burns & Crain, Ltd.

(57) ABSTRACT

Disclosed is a bio-feedback type device for physical pain relief at childbirth, comprising a maternal-fetal monitoring module, a hand-grip pressure transducer, an electrical-stimulation wave group generator, an electrical-stimulation wave group output module and a childbirth pain-relief workstation. The maternal-fetal monitoring module is used for monitoring maternal-fetal vital-sign signals; the hand-grip pressure transducer is used to convert the degree of pain experienced by the mother into a pressure value; the childbirth pain-relief workstation combines and analyzes uterine contraction stress values from the maternal-fetal vital-sign signals with the hand-grip pressure values to produce electrical-stimulation wave group output parameters; on the basis of said output parameters, the electrical-stimulation wave group generator regulates the electrical-stimulation wave group and outputs same to the maternal body surface by means of the electrical-stimulation wave group output module and electrodes; the present invention is also provided with input and display modules to enable interaction between operators and equipment. The present invention is able to provide timely adjustment of electrical-stimulation wave group output parameters, the electrical-stimulation wave group signals taking into account the felt physical reception of different frequencies and waveforms of electrical stimulation pulses.

8 Claims, 9 Drawing Sheets

(56) References Cited

U.S. PATENT DOCUMENTS

| | | | |
|---|---|---|---|
| 8,064,991 B2 * | 11/2011 | Hersh et al. | 600/511 |
| 2007/0233203 A1 * | 10/2007 | Euliano et al. | 607/46 |
| 2011/0184318 A1 | 7/2011 | Kodama | |
| 2013/0046205 A1 | 2/2013 | Schaffner et al. | |

FOREIGN PATENT DOCUMENTS

| | | |
|---|---|---|
| CN | 2862954 | 1/2007 |
| CN | 202086950 | 9/2012 |
| CN | 102940934 | 2/2013 |
| CN | 203280902 | 11/2013 |
| CN | 2737391 | 9/2014 |
| WO | WO 2011080237 | 7/2011 |

OTHER PUBLICATIONS

International Search Report and Written Opinion for Application No. No. PCT/CN2013/087035 dated Nov. 13, 2013.
First Office Action for Priority Chinese Patent Application No. 201210488575.3 mailed on Apr. 22, 2014.
Second Office Action for Priority Chinese Patent Application No. 201210488575.3 mailed on Jul. 24, 2014.
Search Report & Supplementary Search Report for Priority Chinese Patent Application No. 201210488575.3.

* cited by examiner

BIO-FEEDBACK TYPE DEVICE FOR PHYSICAL PAIN RELIEF AT CHILDBIRTH

CROSS REFERENCE TO RELATED APPLICATION

This application is a U.S. National Phase under 35 U.S.C. §371 of International Application No. PCT/CN2013/087035, filed Nov. 13, 2013, which claims priority under 35 U.S.C. §§119 and 365 to Chinese Application No. 201210488575.3, filed Nov. 26, 2012.

FIELD

The present disclosure relates generally to the field of assisted delivery, and more particularly, to a bio-feedback type device for physical pain relief at childbirth.

BACKGROUND

The delivery pain (i.e., labor pain) is second in the pain rating index after burning pain. A severe labor pain may have a negative impact on the physical and mental health of the parturient and the newborn. Many parturients choose cesarean which leads to unnecessary injuries to the body, because they are unable to bear the severe labor pain, or even because they fear the labor pain. There are many reasons causing delivery pain, for example, the paroxysmal contraction of the uterine, the stretching or tearing of muscle fibers of the uterine, and the compression of the vessels of the uterine may trigger pain centers in the brain to make the parturient feel severe pain. When a fetus pass through the birth canal, the fetus may expand the birth canal, especially lower uterine segment, cervix, vagina and perineum, on which damage or traction may occur to cause pain. The nervousness, anxiety or fear of the parturient will cause neuroendocrine responses in the body to amplify the pain.

Due to individual differences, the tolerance and feeling of pain is different for everyone. According to some statistics, about 44 percent of primiparas may feel that the delivery pain is unbearable and even "be dying of pain". This, however, may be correlated with psychogenic factors. Some primiparas feel the delivery pain is not as unbearable as imagine, and they may only feel the distension and pain of the abdomen and the lumbosacral region.

At present, the pain relief at childbirth has the following methods: (1) drug pain relief at childbirth (epidural block), having a reliable analgesic effect, but turning the labor from a physiological process to a pathological process, and needing a specific operation technique, which may affect the fetus and extend the labor, (2) nitrous oxide (i.e., $N_2O$) inhalation, belonging to general anesthesia that the puerperant is required to be fasted, which may depress the cardiovascular system and the central nervous system of the fetus and the newborn; (3) Lamaze breathing, as a psychological analgesia belonging to a mental and psychological therapy; (4) free posture, Doula delivery; (5) transcutaneous electrical nerve stimulation (TENS) pain relief at childbirth, defined as a method for electrically stimulating the skin to reduce pain, by the clinical electrophysiology and American physiological society. The Gate-control theory of pain is one of the theoretical bases for TENS. TENS is a noninvasive way, has a good result with analgesia, does not have side effects on the maternal body and the fetus, and is one of the important non-pharmacological methods for pain relief at childbirth.

There have been many studies about the non-invasive pain relief at childbirth technique. A Chinese utility model patent CN 202086950U, with a publication date of 26 Sep. 2012, discloses a system for pain relief at childbirth, which determines the degree of pain of the parturient according to the signal from the measured blood pressure, sends pulse signals of different pulse widths and strength to stimulate the stomach to sooth the nerve system for analgesia, and plays music and video simultaneously to relieve nervous tension of the parturient to reduce the pain of the parturient. A Chinese utility model patent CN 202086950 U, with a publication date of 28 Dec. 2011, discloses a device for pain relief at childbirth, which combines transcutaneous electric nerve stimulation, pulse therapy and music therapy, while makes use of acupuncture and moxibustion therapy, to provide a green, safe and effective apparatus for pain relief at childbirth. A Chinese utility model patent CN 2737391Y, with a publication date of 29 Sep. 2014, discloses an apparatus for pain relief at childbirth, which generates a series of pulses according to the frequency given by the user, in which the strength of the pulses is adjusted, and the pulses are amplified to be output in isolation by a pulse converter, to act on specific sites of the body to activate the body's own analgesic substance, so as to achieve the purpose of analgesia. A Chinese utility model patent CN 1148989A, with a publication date of 7 May 1997, discloses a computer-based apparatus for pain relief at childbirth and monitoring, which includes an analgesia circuit, a fetal heart sound circuit, a uterine pressure circuit and a fetal movement circuit, simultaneously has the function of analgesia and monitoring, and can give an alarm with sound and light, in which the output of analgesia signals is divides into three channels including a pulse using pulse code modulation (300~600 Hz), a low frequency pulse (2~10 Hz) and a medium frequency pulse (2,000~8,000 Hz), which can be selected by a manual button or automatically controlled based on the strength of uterine contraction. A Chinese utility model patent CN 2216389Y, with a publication date of 3 Jan. 1996, discloses an apparatus for pain relief at childbirth and monitoring with computer, including a control circuit for the strength of the output of the analgesia signals, a monitoring, recording and alarming system for fetal heart sound, and a monitoring and recording system for uterine contraction, which can control the strength of the output of the analgesia signals automatically or manually according to the uterine contraction. A United States utility patent U.S. Pat. No. 7,942,818 B2, with a publication date of 7 May 2011 discloses a method for predicting the time at which a delivery pain happens with signals of uterine contraction.

In the above patent documents related to methods and apparatus for pain relief at childbirth, the degree of the delivery pain is generally determined based on the strength of the uterine contraction, that is, the more strength of the uterine contraction, the greater the amplitude of the wave for stimulating is. And in the above patent documents related to methods and apparatus for pain relief at childbirth, the output wave is a simple pulse signal, and varies only based on the variation of the pulse width, frequency or strength, and there is a single output signal, so the effect of the analgesia is not ideal. In addition, the living body is easy to produce resistance for the single electrical-stimulation that acts on the body for a long time, such that the analgesic effect of the originally effective analgesic stimulation signal will be reduced or even failure after long time.

SUMMARY

In view of the above, a principal object of the present disclosure is to provide a bio-feedback type device for physical pain relief at childbirth, which can determine the degree of the delivery pain more accurately, output a wave group of analgesic electrical-stimulation, and realize maternal-fetal multi-parameter monitoring and pain relief at childbirth synchronously.

According to an aspect of the disclosure, a bio-feedback type device for physical pain relief at childbirth, including a childbirth pain-relief station and an electrical-stimulation wave group output module, wherein the apparatus further includes a maternal-fetal monitoring module, a hand-grip pressure transducer, an electrical-stimulation wave group generator and an electrical-stimulation wave group output module, wherein the maternal-fetal monitoring module, the hand-grip pressure transducer and the electrical-stimulation wave group generator are coupled respectively to the childbirth pain-relief station, and the electrical-stimulation wave group generator is coupled to the electrical-stimulation wave group output module;

the maternal-fetal monitoring module is configured to detect a maternal-fetal physical signal and transmit the detected maternal-fetal physical signal to the childbirth pain-relief station;

the hand-grip pressure transducer is configured to convert a degree of a pain born by a parturient to a hand-grip pressure value and transmit the converted hand-grip pressure value to the childbirth pain-relief station;

the childbirth pain-relief station is configured to regulate an output parameter of electrical-stimulation wave group, analyze a pressure value of uterine contraction in the maternal-fetal physical signal and the hand-grip pressure value from the hand-grip pressure transducer, and calculate the output parameter of electrical-stimulation wave group according to the analyzing; the output parameter of electrical-stimulation wave group including a type, frequency and amplitude of the electrical-stimulation wave group;

the electrical-stimulation wave group generator is configured to generate a corresponding electrical-stimulation wave group according to the output parameter of electrical-stimulation wave group regulated by the childbirth pain-relief station; and the electrical-stimulation wave group output module is configured to output the electrical-stimulation wave group to the parturient's body.

Preferably, regulating the output parameter of electrical-stimulation wave group by the childbirth pain-relief station includes:

step 1, detecting a maximum hand-grip pressure value of the parturient, $F_{max}$, by the hand-grip pressure transducer;

step 2, detecting a real time pressure value of uterine contraction, TOCO, by the maternal-fetal monitoring module;

step 3, detecting a real time hand-grip pressure value of the parturient, F, by the hand-grip pressure transducer; and step 4, originally calculating a type $X_{TOCO}$ and an amplitude $A_{TOCO}$ of the electrical-stimulation wave group according to the TOCO detected in the step 2, and when TOCO>$TOCO_{threshold}$, the type $X_{TOCO}$ of the electrical-stimulation wave group is set to an analgesic wave group, and when TOCO<$TOCO_{threshold}$, the type $X_{TOCO}$ of the electrical-stimulation wave group is a massage wave group, wherein, the $TOCO_{threshold}$ is a pain threshold of uterine contraction pressure, and the amplitude $A_{TOCO}$ of the electrical-stimulation wave group is $A_{TOCO}=K_{TOCO}*TOCO+A_{default}$, wherein $A_{default}$ is a minimum amplitude $A_{min}$, and $K_{TOCO}$ is a proportional coefficient of the amplitude $A_{TOCO}$ of the electrical-stimulation wave group and the real time pressure value of uterine contraction TOCO;

step 5, further calculating a type $X_F$ and an amplitude $A_F$ of the electrical-stimulation wave group according to the real time hand-grip pressure value F detected in the step 3, and when $F<Fk_{threshold}*F_{max}$, $X_F$ is set to $X_{TOCO}$, and the amplitude $A_F$ of the electrical-stimulation wave group is $A=A_{TOCO}+K_F*F+A_{default}$, wherein $Fk_{threshold}$ is a pain threshold of the hand-grip pressure value and meets $Fk_{threshold}>0$, and $K_F$ is a proportional coefficient of the amplitude $A_F$ of the electrical-stimulation wave group and the hand-grip pressure value F; and when $F>Fk_{threshold}*F_{max}$, $X_F$ is set to an analgesic wave group, wherein if the $X_{TOCO}$ is a massage wave group, the amplitude $A_F$ of the electrical-stimulation wave group is $A=K_F*F+A_{default}$, and if the $X_{TOCO}$ is a an analgesic wave group, the amplitude $A_F$ of the electrical-stimulation wave group is $A_F=A_{TOCO}+K_F*F+A_{default}$;

step 6, determining a type X and an amplitude A of the electrical-stimulation wave group final output according to two calculations in the step 4 and the step 5, and synthesizing a final electrical-stimulation wave group according to the final output type X and an amplitude A; and only when both of the $X_{TOCO}$ and the $X_F$ are massage wave groups, the type X of the final electrical-stimulation wave group is set to a massage wave group; in other cases, the type X is set to an analgesic wave group; and the final output amplitude A is set to $A=A_F$, wherein A is less than an upper safety limit of the amplitude $A_{max}$ set by a system.

The electrical-stimulation wave group in the steps 4, 5 and 6 can be divided, according to different clinical effect, into a massage wave group and an analgesic wave group, wherein the massage wave group is an electrical-stimulation wave group which has a main effect of massaging, and the analgesic wave group is an electrical-stimulation wave group which has a main effect of pain relieving.

The electrical-stimulation wave group refers to a kind of wave group combined by modulating carrier waves of different frequencies (150 Hz~10 KHz) with a series of low frequency waves (having a frequency range from 1 Hz to 150 Hz) of different waveform types and different frequency characteristics.

The synthesizing in the step 6 includes:

step 31, setting pattern parameters of each combined basic waveform of a low frequency modulation wave group;

step 32, setting a sequence of combination of each combined basic waveform of the low frequency modulation wave group;

step 33, setting a duration time of each combined basic waveform of the low frequency modulation wave group, combining the combined basic waveforms into a basic wave group, i.e., a low frequency modulation signal;

step 34, setting a corresponding carrier frequency, to obtain a carrier signal;

step 35, modulating the carrier signal in the step 34 with the basic wave group in the step 33 to obtain a first-order wave group;

step 36, repeating steps 31~35, to obtain a plurality of first-order wave groups of different characteristics; and step 37, selecting three to six first-order wave groups obtained in the step 35, and setting a sequence of combination and a duration time to obtain a second-order wave group as an electrical-stimulation wave group.

The pattern parameters in the step 31 include type and frequency. The type of basic waveform includes a trapezoidal wave and a sine wave, and the frequency of the basic waveform has a frequency range from 1 Hz to 150 Hz. The sequence of combination of the basic waveforms in the step 32 means a plurality of basic waves of different frequencies and different types are combined alternately. The combination of the basic wave groups can be divided according to its characteristics and effects, into a massage wave group and an analgesic wave group. The duration time of each combined basic waveform is set by considering feeling and situation of the body about basic waveforms of different frequencies. The waveform of the carrier wave in the step 34 is a sine wave or a square wave, with a frequency range from 150 Hz to 10 KHz. The first-order wave group in the step 35 is obtained by modulating the carrier signal of a high frequency (150 HZ~10 KHz) with a low frequency signal. The difference between the first-order wave groups of different characteristics in the step 36 includes the combination of the basic wave groups, and the frequency of the carrier wave. The sequence of combination in the step 37 means a plurality of first-order wave groups of different carrier frequencies are combined alternately.

Preferably, at least two of the electrical-stimulation wave groups of two types are stored according to the implement parameters in the steps 31~37, in the electrical-stimulation wave group generator in advance, and the childbirth pain-relief station conducts a comprehensive analysis according to the pressure value of uterine contraction from the maternal-fetal monitoring module and hand-grip pressure value from the hand-grip pressure transducer to calculate a output type, frequency and amplitude the electrical-stimulation wave group.

In one preferred embodiment, the electrical-stimulation wave group generator includes a waveform sampled data storage unit, a frequency storage unit, an amplitude storage unit, a data reading unit, a D/A converter and an amplifying-driving circuit, wherein the waveform sampled data storage unit is configured to store sampled data of a cycle of carrier signal, the frequency storage unit is configured to store a real-time frequency of the electrical-stimulation wave group, the amplitude storage unit is configured to store a real-time amplitude of the electrical-stimulation wave group, the data reading unit data reading unit is configured to circularly read the waveform sampled data storage unit at the frequency stored in the frequency storage unit, and circularly output waveform sampled data in sequence, the D/A converter is configured to convert the waveform sampled data to analog signal, and the amplifying-driving circuit is configured to adjust the electrical-stimulation wave group to be output according to the amplitude stored in the amplitude storage unit.

Preferably, the sampled data of at least two of the electrical-stimulation wave groups of two types is stored in the electrical-stimulation wave group generator in advance, the childbirth pain-relief station conducts a comprehensive analysis according to the pressure value of uterine contraction from the maternal-fetal monitoring module and hand-grip pressure value from the hand-grip pressure transducer to calculate an output type, frequency and amplitude the electrical-stimulation wave group.

In another preferred embodiment, the electrical-stimulation wave group generator includes a wave group sampled database, a microcomputer system, D/A converter and an amplifying-driving circuit connected in sequence, wherein the wave group sampled database is provided in a storage medium, and configured to store the sampled data of at least two of the electrical-stimulation wave groups, the microcomputer system is configured to sequentially read wave group sampled data of a corresponding type from the wave group sampled database at a sampling frequency of the electrical-stimulation wave group, according to the output type of the electrical-stimulation wave group calculated by the childbirth pain-relief station, the D/A converter is configured to convert the wave group sampled data to an electrical-stimulation wave group, and the amplifying-driving circuit is configured to adjust the electrical-stimulation wave group to be output according to the output amplitude of the electrical-stimulation wave group calculated by the childbirth pain-relief station.

In a further preferred embodiment, the electrical-stimulation wave group generator includes a wave group sampled data memory, an automatic scanning circuit, D/A converter and an amplifying-driving circuit connected in sequence, wherein the wave group sampled data memory is configured to store the sampled data of at least two of the electrical-stimulation wave groups, the automatic scanning circuit is configured to generate address information with a digital logic circuit, and scan a waveform data storage unit a corresponding type at a sampling frequency of the electrical-stimulation wave group to make the memory output wave group sampled data in turn, according to the output type of the electrical-stimulation wave group calculated by the childbirth pain-relief station, the D/A converter is configured to convert the wave group sampled data to an electrical-stimulation wave group, and the amplifying-driving circuit is configured to adjust the electrical-stimulation wave group to be output according to the output amplitude of the electrical-stimulation wave group calculated by the childbirth pain-relief station.

Compared with the prior art, the present disclosure has the following advantages and effects.

Firstly, the hand-grip pressure transducer can continuously reflect the feeling and endurance of the parturient about the pain more accurately, and compared with the existing technical solution of adjusting the amplifier gain by a bottom, it is more practical and effective. Because it is quite natural that the parturient may clench her hands when she feels pain, the pressure signal can reflect the feeling of the parturient about the pain continuously and accurately.

Secondly, the electrical-stimulation wave group is output by considering the different feeling of people about electrical-stimulation pulses of different frequencies and waveforms to obtain a better effect. The basic waveforms of alternately varied frequencies are combined into a basic wave group, the basic wave group modulates carrier signals of different frequencies to obtain a first-order wave group, and a plurality of first-order wave groups of alternately varied carrier frequencies are combined into a second-order wave group, i.e., electrical-stimulation wave group.

Thirdly, compared with the prior art, the determination of the delivery pain according to the disclosure takes into account of the diversity of the feeling of the parturient about the pain. The disclosure can estimate the feeling degree of the parturient about the pain more accurately by synthetically analyzing the uterine contraction of the parturient and the pressure feedback signal from the hand-grip pressure transducer, and the feeling degree as a biological feedback will be classified for hierarchical control, to has a better result with analgesia and overcome the resistance for the single electrical-stimulation that acts on the parturient for a long time.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE PREFERRED EMBODIMENTS

In the following description of embodiments, reference is made to the accompanying drawings which form a part hereof, and in which it is shown by way of illustration specific embodiments of the disclosure that can be practiced. It is to be understood that other embodiments can be used and structural changes can be made without departing from the scope of the disclosed embodiments.

Example One

Figure 1:
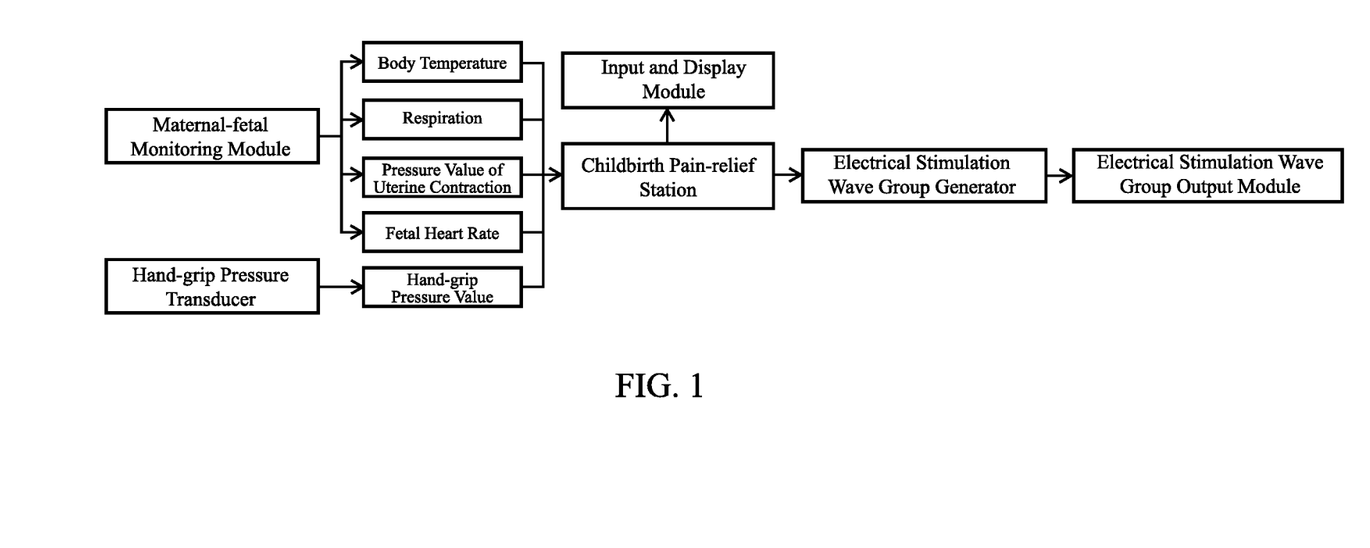
FIG. 1 is a schematic diagram illustrating a bio-feedback type device for physical pain relief at childbirth according to one embodiment of the present disclosure.

As shown in FIG. 1, a bio-feedback type device for physical pain relief at childbirth includes a maternal-fetal monitoring module, a hand-grip pressure transducer, an electrical-stimulation wave group generator, an electrical-stimulation wave group output module, an input and display module and a childbirth pain-relief station, wherein the maternal-fetal monitoring module, the hand-grip pressure transducer, the electrical-stimulation wave group generator and the input and display module are coupled to the childbirth pain-relief station respectively, and the electrical-stimulation wave group generator is coupled to the electrical-stimulation wave group output module.

The maternal-fetal monitoring module is configured to detect a physical signal of a parturient and a fetus (hereafter referred to as a maternal-fetal physical signal) and transmit the detected maternal-fetal physical signal to the childbirth pain-relief station. The maternal-fetal physical signal is selected from the group consisting of electrocardiosignal, blood pressure, oxyhemoglobin saturation, pulse, body temperature, breathe, fetal heart rate and pressure value of uterine contraction.

the hand-grip pressure transducer is configured to convert a degree of a pain born by a parturient to a hand-grip pressure value and transmit the converted hand-grip pressure value to the childbirth pain-relief station;

the childbirth pain-relief station is configured to regulate an output parameter of electrical-stimulation wave group, analyze a pressure value of uterine contraction in the maternal-fetal physical signal and the hand-grip pressure value from the hand-grip pressure transducer, and calculate the output parameter of electrical-stimulation wave group according to the analyzing;

the output parameter of electrical-stimulation wave group including a type, frequency and amplitude of the electrical-stimulation wave group;

the electrical-stimulation wave group generator is configured to generate a corresponding electrical-stimulation wave group according to the output parameter of electrical-stimulation wave group regulated by the childbirth pain-relief station; and the electrical-stimulation wave group output module is configured to output the electrical-stimulation wave group to the parturient's body.

The input and display module configured to interact with an operator or a device, including inputting the parameters of the maternal-fetal monitoring module, inputting of the parameters of electrical-stimulation wave group generator and display of the maternal-fetal physical parameters and their waveforms. The input parameters of the maternal-fetal monitoring module include an alarm setting of the maternal-fetal monitoring module and zero setting of the uterine contraction pressure. The input parameters of the electrical-stimulation wave group generator include type, frequency and amplitude of the electrical-stimulation wave group.

In the embodiment, the electrical-stimulation wave group output module includes an electrical-stimulation wave group output electrode and a cable coupled to the electrical-stimulation wave group generator.

Figure 2:
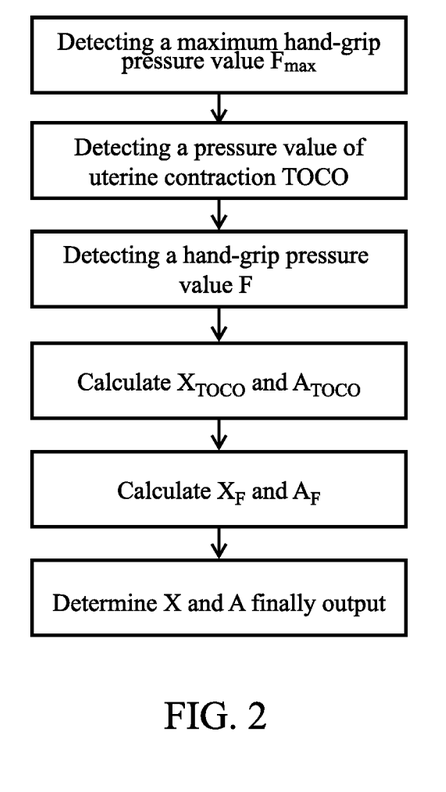
FIG. 2 is a schematic diagram illustrating a method for adjustment of parameters of a bio-feedback type device for physical pain relief at childbirth according to one embodiment of the present disclosure.

As shown in FIG. 2, regulating the output parameter of electrical-stimulation wave group by the childbirth pain-relief station in the bio-feedback type device for physical pain relief at childbirth includes:

step 1, detecting a maximum hand-grip pressure value of the parturient, denoted by $F_{max}$, by the hand-grip pressure transducer;

step 2, detecting a real time pressure value of uterine contraction, denoted by TOCO, by the maternal-fetal monitoring module;

step 3, detecting a real time hand-grip pressure value of the parturient, denoted by F, by the hand-grip pressure transducer, and step 4, originally calculating a type $X_{TOCO}$ and an amplitude $A_{TOCO}$ of the electrical-stimulation wave group according to the TOCO detected in the step 2, and when $TOCO > TOCO_{threshold}$, the type $X_{TOCO}$ of the electrical-stimulation wave group is set to an analgesic wave group, while when $TOCO < TOCO_{threshold}$, the type $X_{TOCO}$ of the electrical-stimulation wave group is a massage wave group, wherein, the $TOCO_{threshold}$ is a pain threshold of uterine contraction pressure, and the amplitude $A_{TOCO}$ of the electrical-stimulation wave group is $A_{TOCO} = K_{TOCO} * TOCO + A_{default}$, wherein $A_{default}$ is a minimum amplitude $A_{min}$, and $K_{TOCO}$ is a proportional coefficient of the amplitude $A_{TOCO}$ of the electrical-stimulation wave group and the real time pressure value of uterine contraction TOCO;

step 5, further calculating a type $X_F$ and an amplitude $A_F$ of the electrical-stimulation wave group according to the real time hand-grip pressure value F detected in the step 3, and when $F < Fk_{threshold} * F_{max}$, $X_F$ is set to $X_{TOCO}$, and the amplitude $A_F$ of the electrical-stimulation wave group is $A_F = A_{TOCO} + K_F * F + A_{default}$, wherein $Fk_{threshold}$ is a, $Fk_{threshold}$ is a pain threshold of the hand-grip pressure value and meets $Fk_{threshold}>0$, and $K_F$ is a proportional coefficient of the amplitude $A_F$ of the electrical-stimulation wave group and the hand-grip pressure value F; and when $F>Fk_{threshold}*F_{max}$, $X_F$ is set to an analgesic wave group, wherein if the $X_{TOCO}$ is a massage wave group at this point, the amplitude $A_F$ of the electrical-stimulation wave group is $A_F=K_F*F+A_{default}$, and if the $X_{TOCO}$ is a an analgesic wave group, the amplitude $A_F$ of the electrical-stimulation wave group is $A_F=A_{TOCO}+K_F*F+A_{default}$;

step 6, determining a type X and an amplitude A of the electrical-stimulation wave group final output according to two calculations in the step 4 and the step 5, and synthesizing a final electrical-stimulation wave group according to the final output type X and an amplitude A; and only when both of the $X_{TOCO}$ and the $X_F$ are massage wave groups, the type X of the final electrical-stimulation wave group is set to a massage wave group; in other cases, the type X is set to an analgesic wave group; and the final output amplitude A is set to $A=A_F$, wherein A is less than an upper limit of the amplitude $A_{max}$ set by a system.

The electrical-stimulation wave group in the steps 4, 5 and 6 can be divided according to different clinical effect, into a massage wave group and an analgesic wave group, wherein the massage wave group is an electrical-stimulation wave group taking massage as a main effect, and the analgesic wave group is an electrical-stimulation wave group taking relieving pain as a main effect.

The electrical-stimulation wave group refers to a kind of wave group combined by modulating carrier waves of different frequencies (150 Hz~10 KHz) with a series of low frequency waves (having a frequency range from 1 Hz to 150 Hz) of different waveform types and different frequency characteristics.

The calculation and/or selection of the type and amplitude of the electrical-stimulation wave group in the steps 4-6 can be implemented by the childbirth pain-relief station. The childbirth pain-relief station also transmits the type and amplitude for the final output to the electrical-stimulation wave group generator.

Figure 3:
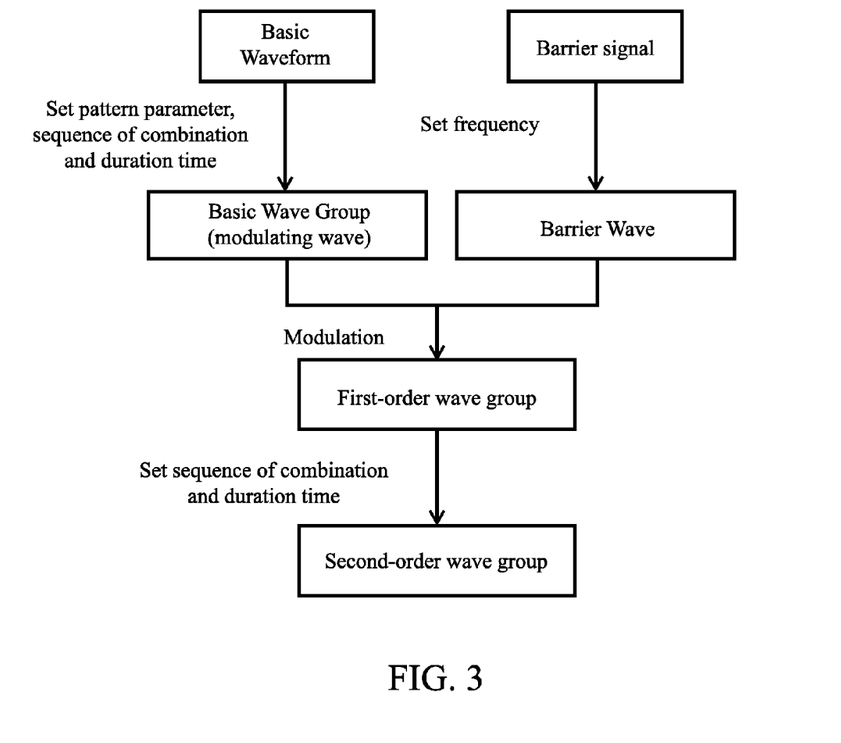
FIG. 3 is a schematic diagram illustrating an implementation process of an electrical-stimulation wave group according to one embodiment of the present disclosure.

As shown in FIG. 3, the implementation process of an electrical-stimulation wave group includes:

step 31, setting pattern parameters of each combined basic waveform of a low frequency modulation wave group;

step 32, setting a sequence of combination of each combined basic waveform of the low frequency modulation wave group;

step 33, setting a duration time of each combined basic waveform of the low frequency modulation wave group, combining the combined basic waveforms into a basic wave group, i.e., a low frequency modulation signal;

step 34, setting a corresponding carrier frequency, to obtain a carrier signal;

step 35, modulating the carrier signal in the step 34 with the basic wave group in the step 33 to obtain a first-order wave group;

step 36, repeating steps 31~35, to obtain a plurality of first-order wave groups of different characteristics; and step 37, selecting three to six first-order wave groups obtained in the step 35, and setting a sequence of combination and a duration time to obtain a second-order wave group as an electrical-stimulation wave group.

The pattern parameters in the step 31 include a type and a frequency. The type of basic waveform includes a trapezoidal wave and a sine wave, and the frequency of the basic waveform has a frequency range from 1 Hz to 150 Hz. The sequence of combination of the basic waveforms in the step 32 means a plurality of basic waves of different frequencies and different types are combined alternately. The combination of the basic wave groups can be divided according to its characteristics and effects, into a massage wave group and an analgesic wave group. The duration time of each combined basic waveform is set by considering feeling and situation of the body about basic waveforms of different frequencies. The waveform of the carrier wave in the step 34 is a sine wave or a square wave, with a frequency range from 150 Hz to 10 KHz. The first-order wave group in the step 35 is obtained by modulating the carrier signal of a high frequency (150 HZ~10 KHz) with a low frequency signal. The difference between the first-order wave groups of different characteristics in the step 36 includes the combination of the basic wave groups, and the frequency of the carrier wave. The sequence of combination in the step 37 means a plurality of first-order wave groups of different carrier frequencies are combined alternately.

Figure 4:
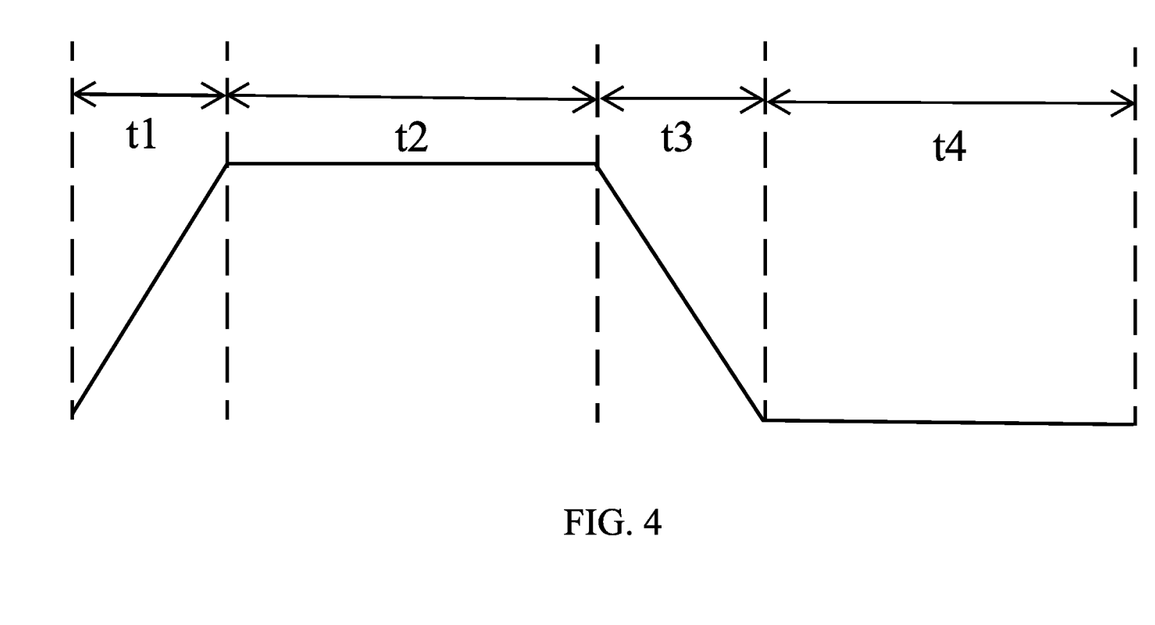
FIG. 4 is a schematic diagram illustrating an implementation process of a basic waveform according to one embodiment of the present disclosure.

As shown in FIG. 4, in the embodiment, the pattern of the basic waveform in the step 31 is a trapezoidal wave, and the waveform parameters are represented by a rising edge duration time t1, a high level duration time t2, a falling edge duration time t3 and a low level duration time t4. A variety of basic waveforms of different frequencies and types can be obtained according to the length of each duration time.

Figure 5:
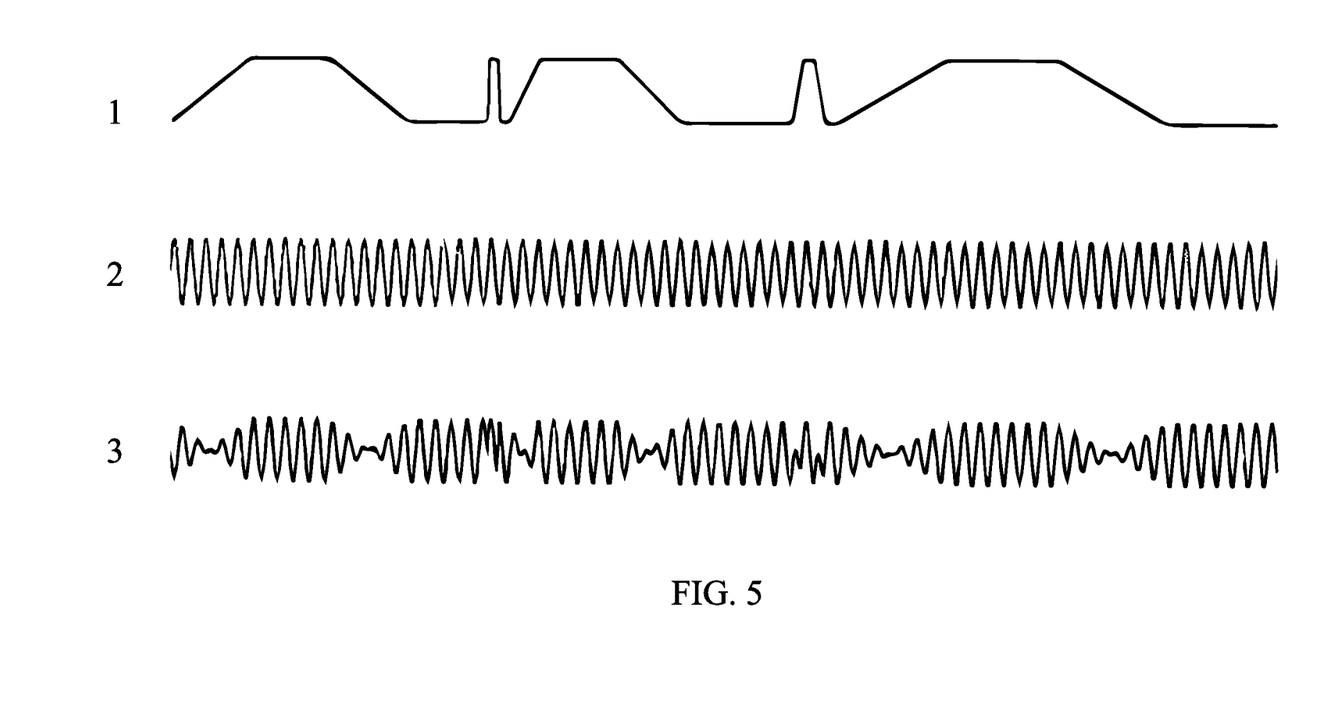
FIG. 5 is a schematic diagram illustrating a plurality of basic wave group combining a first-order wave group according to one embodiment of the present disclosure.

As shown in FIG. 5, in the embodiment, the settings of the first-order wave group 3 in the steps 32 and 33 can be represented as: $n_1$ (First Basic Waveform)+$n_2$ (Second Basic Waveform)+$n_3$ (Third Basic Waveform)+$n_4$ (Fourth Basic Waveform)+$n_5$ (Fifth Basic Waveform), meaning that the basic wave group 1 is combined by $n_1$ first basic waveforms, $n_2$ second basic waveforms, $n_3$ third basic waveforms, $n_4$ fourth basic waveforms and $n_5$ fifth basic waveforms, wherein $n_1$, $n_2$, $n_3$, $n_4$ and $n_5$ are integers. FIG. 5 shows a cycle of the basic waveform. The duration time of the basic waveform is determined by the frequency and number of the basic waveforms. The frequency of the carrier wave 2 is set in the step 34, and the carrier wave 2 is modulated by the basic wave group 1 to obtain a first-order wave group 3 in the step 35.

Figure 6:
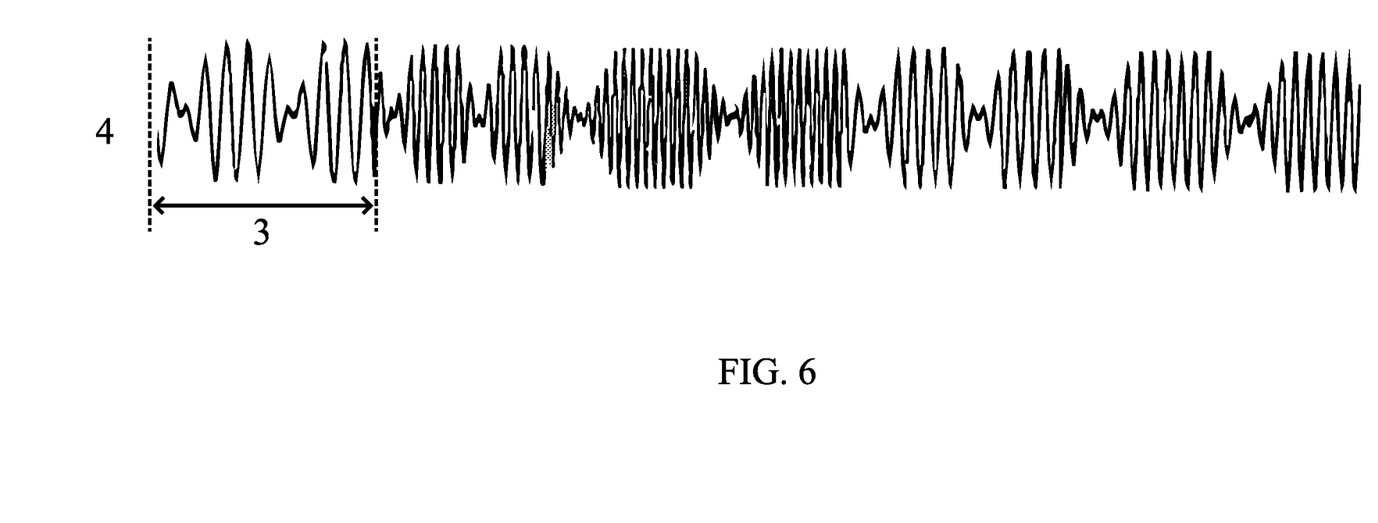
FIG. 6 is a schematic diagram illustrating an implementation process of a second-order wave group according to one embodiment of the present disclosure.

As shown in FIG. 6, in the embodiment, the settings of the second-order wave group 4 in the steps 36 and 37 can be represented as: $m_1$ (First First-order Wave Group)+$m_2$ (Second First-order Wave Group)+$m_3$ (Third First-order Wave Group)+$m_4$ (Fourth First-order Wave Group)+$m_5$ (Fifth First-order Wave Group), meaning that the second-order wave group is combined by $n_1$ first first-order wave groups, $n_2$ second first-order wave groups, $n_3$ third first-order wave groups, $n_4$ fourth first-order wave groups and $n_5$ fifth first-order wave groups, wherein $n_1$, $n_2$, $n_3$, $n_4$ and $n_5$ are integers. FIG. 6 shows a cycle of the first-order wave group.

In the embodiment, there is a set of parameters of the wave group for a good analgesic effect as follows. For the basic waveform, the rising edge duration time t1 and the falling edge duration time t3 are zero, and the high level duration time t2 and the low level duration time t4 are half of the period respective. There are eight basic waveforms of different frequencies including 2 Hz, 5 Hz, 10 Hz, 20 Hz, 25 Hz, 50 Hz, 75 Hz and 100 Hz, and the corresponding periods are 500 ms, 200 ms, 100 ms, 50 ms, 40 ms, 20 ms, 13.3 ms and 10 ms respectively. The analgesic wave groups output to the hands and waist of the parturient are implemented by different first-order wave groups, but in order to make the hands and waist have the same feeling, the carrier frequencies output to the hands and waist at the same time are the same.

First basic wave group: total duration time: 15 seconds, and carrier frequency: 1 KHz.

Waist: 10 (2 Hz)+192 (5 Hz)+128 (50 Hz)+64 (25 Hz)+255 (100 Hz)

Hand: 10 (2 Hz)+192 (75 Hz)+128 (50 Hz)+64 (25 Hz)+255 (100 Hz)

Second basic wave group: total duration time: 11.6 seconds, and carrier frequency: 2.5 KHz.

Waist: 15 (5 Hz)+80 (5 Hz)+10 (2 Hz)+80 (100 Hz)+20 (10 Hz)

Hand: 15 (2 Hz)+40 (50 Hz)+10 (2 Hz)+40 (50 Hz)+20 (10 Hz)

Third basic wave group: total duration time: 21 seconds, and carrier frequency: 2.5 KHz.

Waist: 20 (2 Hz)+300 (75 Hz)+99 (25 Hz)+200 (100 Hz)+50 (50 Hz)

Hand: 20 (2 Hz)+200 (50 Hz)+990 (25 Hz)+50 (100 Hz)+125 (50 Hz)

Fourth basic wave group: total duration time: 9.5 seconds, and carrier frequency: 2.5 KHz.

Waist: 10 (2 Hz)+50 (20 Hz)+198 (100 Hz)

Hand: 10 (2 Hz)+50 (20 Hz)+99 (50 Hz)

Fifth basic wave group: total duration time: 28 seconds, and carrier frequency: 1 KHz.

Waist: 30 (2 Hz)+300 (75 Hz)+99 (25 Hz)+300 (100 Hz)+90 (50 Hz)

Hand: 30 (2 Hz)+300 (75 Hz)+990 (25 Hz)+80 (100 Hz)+200 (50 Hz)

Sixth basic wave group: total duration time: 9.5 seconds, and carrier frequency: 1 KHz.

Waist: 10 (2 Hz)+50 (20 Hz)+198 (100 Hz)

Hand: 10 (2 Hz)+50 (20 Hz)+99 (50 Hz)

By modulating corresponding carrier waves with the above first to sixth basic wave groups, two better electrical-stimulation wave groups can be obtained as below.

First second-order wave group: 42 (Third first-order wave group)+38 (Fourth first-order wave group)+56 (Fifth first-order wave group)+24 (Second first-order wave group)+45 (First first-order wave group)

Second second-order wave group: 42 (Third first-order wave group)+38 (Sixth first-order wave group)+24 (Second first-order wave group)+56 (Fifth first-order wave group)+38 (Fourth first-order wave group)+45 (First first-order wave group)

At least two of the electrical-stimulation wave groups of two types are stored according to the implement parameters in the steps 31~37, in the electrical-stimulation wave group generator in advance, and the childbirth pain-relief station conducts a comprehensive analysis according to the pressure value of uterine contraction from the maternal-fetal monitoring module and hand-grip pressure value from the hand-grip pressure transducer to calculate a output type, frequency and amplitude the electrical-stimulation wave group.

Figure 7:
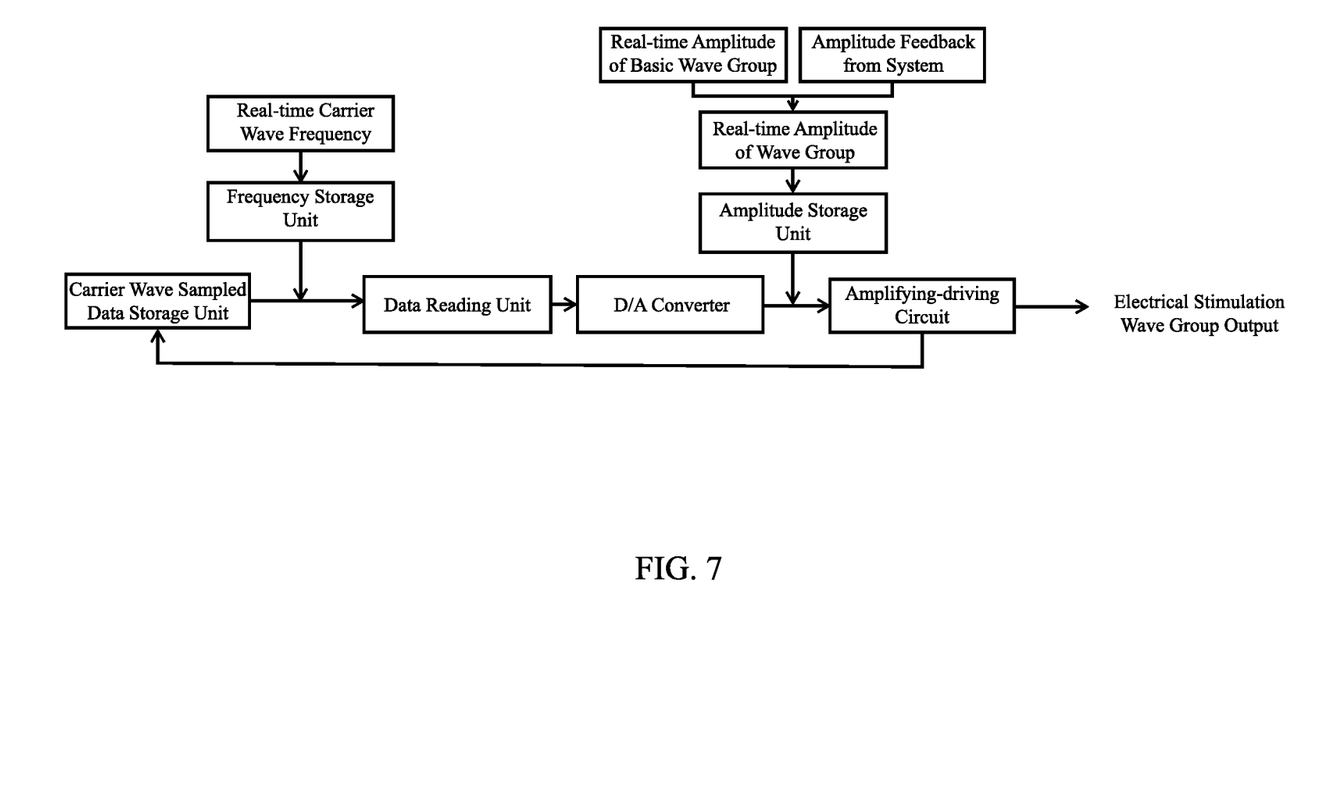
FIG. 7 is a schematic diagram illustrating an electrical-stimulation wave group generator according to one embodiment of the present disclosure.

In the embodiment, as shown in FIG. 7, the electrical-stimulation wave group generator includes a waveform sampled data storage unit, a frequency storage unit, an amplitude storage unit, a data reading unit, a D/A converter and an amplifying-driving circuit. The real-time frequency and amplitude of the electrical-stimulation wave group are calculated based on the output type and amplitude of the electrical-stimulation wave group calculated buy the childbirth pain-relief station as follows. (1) The real-time frequency of the electrical-stimulation wave group is calculated based on the implement parameters of the electrical-stimulation wave group corresponding to the output type of the electrical-stimulation wave group calculated by the childbirth pain-relief station, that is, the real-time frequency of the electrical-stimulation wave group is equal to the real-time frequency of the carrier signal stored in the step 34 in advance; and (2) the real-time amplitude of the electrical-stimulation wave group is calculated based on the implement parameters of the electrical-stimulation wave group corresponding to the output type of the electrical-stimulation wave group calculated by the childbirth pain-relief station, and based on the output amplitude of the amplitude calculated by the childbirth pain-relief station, that is, the real-time amplitude of the electrical-stimulation wave group is calculated based on the pattern parameters stored in the step 31, the sequence of combination stored in the step 32 and the duration time stored in the step 33 in advance, and the real-time amplitude of the electrical-stimulation wave group is equal to the real-time amplitude of the basic wave group times the amplitude of the electrical-stimulation wave group stored in advance. The waveform sampled data storage unit is configured to store sampled data of a cycle of carrier signal, the frequency storage unit is configured to store a real-time frequency of the electrical-stimulation wave group, the amplitude storage unit is configured to store a real-time amplitude of the electrical-stimulation wave group, the data reading unit data reading unit is configured to circularly read the waveform sampled data storage unit at the frequency stored in the frequency storage unit, and circularly output waveform sampled data in sequence, the D/A converter is configured to convert the waveform sampled data to analog signal, and the amplifying-driving circuit is configured to adjust the electrical-stimulation wave group to be output according to the amplitude stored in the amplitude storage unit.

Example Two

The example is similar to Example One, excepting that the sampled data of the electrical-stimulation wave group itself is stored in the electrical-stimulation wave group generator in advance, and it is selected for output according to actual need, as follows. At least two of the electrical-stimulation wave groups of two types are stored in the electrical-stimulation wave group generator in advance, and the childbirth pain-relief station conducts a comprehensive analysis according to the pressure value of uterine contraction from the maternal-fetal monitoring module and hand-grip pressure value from the hand-grip pressure transducer to calculate the output type, frequency and amplitude the electrical-stimulation wave group.

Figure 8:
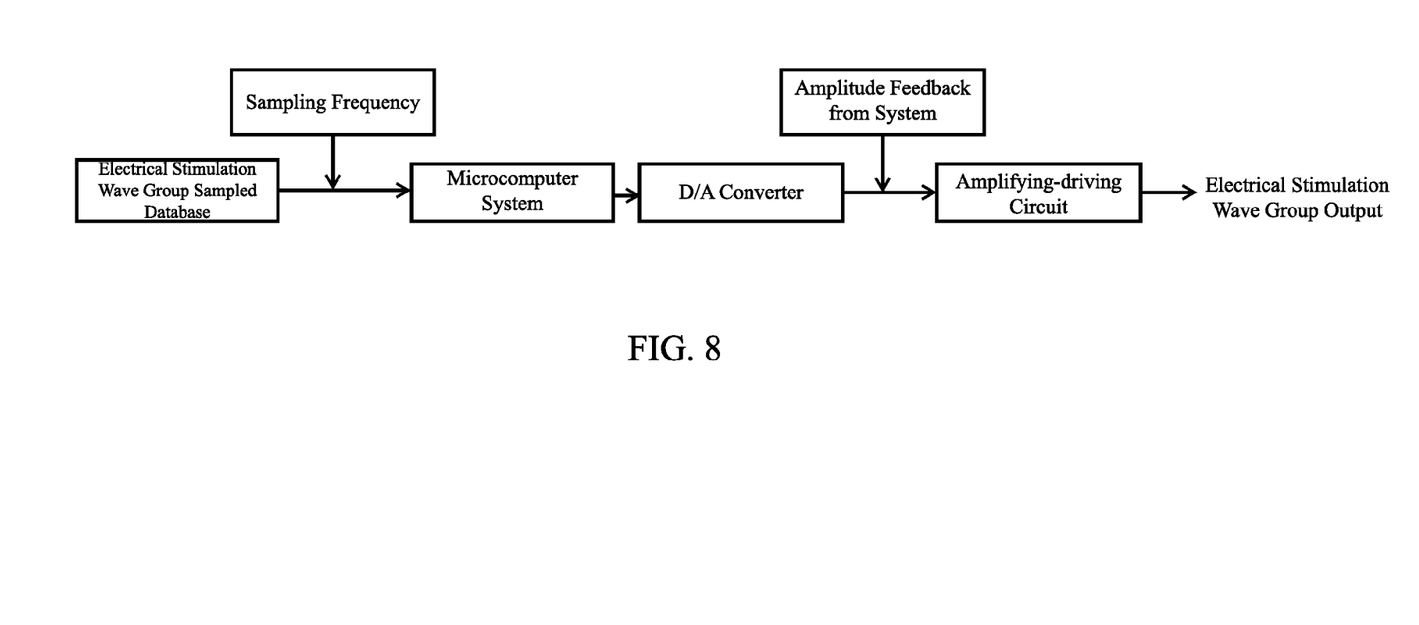
FIG. 8 is a schematic diagram illustrating an electrical-stimulation wave group generator according to another embodiment of the present disclosure.

As shown in FIG. 8, the electrical-stimulation wave group generator includes a wave group sampled database, a microcomputer system, D/A converter and an amplifying-driving circuit connected in sequence. The wave group sampled database is provided in a storage medium selected from the group consisting of magnetic disk, optical disc, USB flash disk, CF card and SD card, and configured to store the sampled data of at least two of the electrical-stimulation wave groups, the microcomputer system is configured to sequentially read wave group sampled data of a corresponding type from the wave group sampled database at a sampling frequency of the electrical-stimulation wave group, according to the output type of the electrical-stimulation wave group calculated by the childbirth pain-relief station, the D/A converter is configured to convert the wave group sampled data to an electrical-stimulation wave group, and the amplifying-driving circuit is configured to adjust the electrical-stimulation wave group to be output according to the output amplitude of the electrical-stimulation wave group calculated by the childbirth pain-relief station.

Example Three

The example is similar to Example One, excepting that excepting that the sampled data of the electrical-stimulation wave group itself is stored in the electrical-stimulation wave group generator in advance, and it is selected for output according to actual need, as follows. At least two of the electrical-stimulation wave groups of two types are stored in the electrical-stimulation wave group generator in advance, and the childbirth pain-relief station conducts a comprehensive analysis according to the pressure value of uterine contraction from the maternal-fetal monitoring module and hand-grip pressure value from the hand-grip pressure transducer to calculate the output type, frequency and amplitude the electrical-stimulation wave group.

Figure 9:
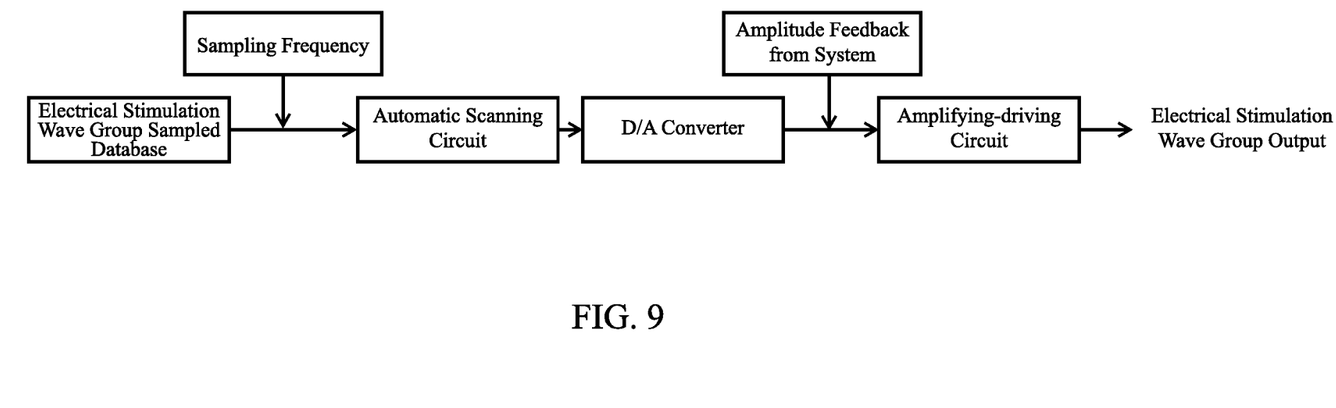
FIG. 9 is a schematic diagram illustrating an electrical-stimulation wave group generator according to a further embodiment of the present disclosure.

As shown in FIG. 9, the electrical-stimulation wave group generator includes a wave group sampled data memory, an automatic scanning circuit, D/A converter and an amplifying-driving circuit connected in sequence. The wave group sampled data memory is selected from the group consisting of ROM, PROM, PROM, E$^2$PROM and flash memory, and is configured to store the sampled data of at least two of the electrical-stimulation wave groups, the automatic scanning circuit is configured to generate address information with a digital logic circuit, and scan a waveform data storage unit a corresponding type at a sampling frequency of the electrical-stimulation wave group to make the memory output wave group sampled data in turn, according to the output type of the electrical-stimulation wave group calculated by the childbirth pain-relief station, the D/A converter is configured to convert the wave group sampled data to an electrical-stimulation wave group, and the amplifying-driving circuit is configured to adjust the electrical-stimulation wave group to be output according to the output amplitude of the electrical-stimulation wave group calculated by the childbirth pain-relief station.

In other embodiments, the implement parameters of the electrical-stimulation wave group or the type, frequency and amplitude of the electrical-stimulation wave group can also be manually set, and the device according to Example One to Three outputs the electrical-stimulation wave group.

The above embodiments are chosen and described in order to explain the principles of the disclosure and their practical application so as to activate others skilled in the art to utilize the disclosure. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A bio-feedback type device for physical pain relief at childbirth, comprising a childbirth pain-relief station and an electrical-stimulation wave group output module, wherein the apparatus further comprising a maternal-fetal monitoring module, a hand-grip pressure transducer, an electrical-stimulation wave group generator and an electrical-stimulation wave group output module; the maternal-fetal monitoring module, the hand-grip pressure transducer and the electrical-stimulation wave group generator are coupled respectively to the childbirth pain-relief station, and the electrical-stimulation wave group generator is coupled to the electrical-stimulation wave group output module;

the maternal-fetal monitoring module is configured to detect a maternal-fetal physical signal and transmit the detected maternal-fetal physical signal to the childbirth pain-relief station;

the hand-grip pressure transducer is configured to convert a degree of a pain born by a parturient to a hand-grip pressure value and transmit the converted hand-grip pressure value to the childbirth pain-relief station;

the childbirth pain-relief station is configured to regulate an output parameter of electrical-stimulation wave group by analyzing a pressure value of uterine contraction in the maternal-fetal physical signal and the hand-grip pressure value from the hand-grip pressure transducer, and calculating the output parameter of electrical-stimulation wave group according to the analyzing; the output parameter of electrical-stimulation wave group including type, frequency and amplitude of the electrical-stimulation wave group;

the electrical-stimulation wave group generator is configured to generate a corresponding electrical-stimulation wave group according to the output parameter of electrical-stimulation wave group regulated by the childbirth pain-relief station, and the electrical-stimulation wave group output module is configured to output the electrical-stimulation wave group to the parturient's body.

2. The bio-feedback type device for physical pain relief at childbirth of claim 1, wherein regulating the output parameter of electrical-stimulation wave group by the childbirth pain-relief station comprises:

step 1, detecting a maximum hand-grip pressure value of the parturient, $F_{max}$, by the hand-grip pressure transducer;

step 2, detecting a real time pressure value of uterine contraction, TOCO, by the maternal-fetal monitoring module;

step 3, detecting a real time hand-grip pressure value of the parturient, F, by the hand-grip pressure transducer; and step 4, originally calculating a type $X_{TOCO}$ and an amplitude $A_{TOCO}$ of the electrical-stimulation wave group according to the TOCO detected in the step 2, and when $TOCO > TOCO_{threshold}$, the type $X_{TOCO}$ of the electrical-stimulation wave group is set to an analgesic wave group, and when $TOCO < TOCO_{threshold}$, the type $X_{TOCO}$ of the electrical-stimulation wave group is a massage wave group, wherein, the $TOCO_{threshold}$ is a pain threshold of uterine contraction pressure, and the amplitude $A_{TOCO}$ of the electrical-stimulation wave group is $A_{TOCO} = K_{TOCO} * TOCO + A_{default}$, wherein $A_{default}$ is a minimum amplitude $A_{min}$, and $K_{TOCO}$ is a proportional coefficient of the amplitude $A_{TOCO}$ of the electrical-stimulation wave group and the real time pressure value of uterine contraction TOCO;

step 5, further calculating a type $X_F$ and an amplitude $A_F$ of the electrical-stimulation wave group according to the real time hand-grip pressure value F detected in the step 3, and when $F < Fk_{threshold} * F_{max}$, $X_F$ is set to $X_{TOCO}$, and the amplitude $A_F$ of the electrical-stimulation wave group is $A_F = A_{TOCO} + K_F * F + A_{default}$, wherein $Fk_{threshold}$ is a pain threshold of the hand-grip pressure value and meets $Fk_{threshold} > 0$, and $K_F$ is a proportional coefficient of the amplitude $A_F$ of the electrical-stimulation wave group and the hand-grip pressure value F; and when $F > Fk_{threshold} * F_{max}$, $X_F$ is set to an analgesic wave group, wherein if the $X_{TOCO}$ is a massage wave group, the amplitude $A_F$ of the electrical-stimulation wave group is $A_F = K_F * F + A_{default}$, and if the $X_{TOCO}$ is a an analgesic wave group, the amplitude $A_F$ of the electrical-stimulation wave group is $A_F = A_{TOCO} + K_F * F + A_{default}$;

step 6, determining a final output type X and amplitude A of the electrical-stimulation wave group according to two calculations in the step 4 and the step 5, and synthesizing a final electrical-stimulation wave group according to the final output type X and an amplitude A; and only when both of the $X_{TOCO}$ and the $X_F$ are massage wave groups, the type X of the final electrical-stimulation wave group is set to a massage wave group; in other cases, the type X is set to an analgesic wave group; and the final output amplitude A is set to $A=A_F$, wherein A is less than an upper safety limit of the amplitude $A_{max}$ set by a system.

3. The bio-feedback type device for physical pain relief at childbirth of claim 2, wherein the synthesizing in the step 6 comprising:

step 31, setting pattern parameters of each combined basic waveform of a low frequency modulation wave group;

step 32, setting a sequence of combination of each combined basic waveform of the low frequency modulation wave group;

step 33, setting a duration time of each combined basic waveform of the low frequency modulation wave group, combining the basic waveforms into a basic wave group, i.e., a low frequency modulation signal;

step 34, setting a corresponding carrier frequency, to obtain a carrier signal;

step 35, modulating the carrier signal in the step 34 with the basic wave group in the step 33 to obtain a first-order wave group;

step 36, repeating steps 31~35, to obtain a plurality of first-order wave groups of different characteristics; and step 37, selecting three to six first-order wave groups obtained in the step 35, and setting a sequence of combination and a duration time to obtain a second-order wave group as an electrical-stimulation wave group.

4. The bio-feedback type device for physical pain relief at childbirth of claim 3, wherein the basic waveform has a frequency range from 1 Hz to 150 Hz, and the waveform of the carrier wave is a sine wave or a square wave, with a frequency range from 150 Hz to 10 KHz.

5. The bio-feedback type device for physical pain relief at childbirth of claim 1, wherein the electrical-stimulation wave group generator comprises a waveform sampled data storage unit, a frequency storage unit, an amplitude storage unit, a data reading unit, a D/A converter and an amplifying-driving circuit, wherein the waveform sampled data storage unit is configured to store sampled data of a cycle of carrier signal, the frequency storage unit is configured to store a real-time frequency of the electrical-stimulation wave group, the amplitude storage unit is configured to store a real-time amplitude of the electrical-stimulation wave group, the data reading unit data reading unit is configured to circularly read the waveform sampled data storage unit at the frequency stored in the frequency storage unit, and circularly output waveform sampled data in sequence, the D/A converter is configured to convert the waveform sampled data to analog signal, and the amplifying-driving circuit is configured to adjust the electrical-stimulation wave group to be output according to the amplitude stored in the amplitude storage unit.

6. The bio-feedback type device for physical pain relief at childbirth of claim 1, wherein the electrical-stimulation wave group generator comprises a wave group sampled database, a microcomputer system, a D/A converter and an amplifying-driving circuit connected in sequence, wherein the wave group sampled database is provided in a storage medium, and configured to store the sampled data of at least two of the electrical-stimulation wave groups; the microcomputer system is configured to sequentially read wave group sampled data of a corresponding type from the wave group sampled database at a sampling frequency of the electrical-stimulation wave group, according to the output type of the electrical-stimulation wave group calculated by the childbirth pain-relief station; the D/A converter is configured to convert the wave group sampled data to an electrical-stimulation wave group; and the amplifying-driving circuit is configured to adjust the electrical-stimulation wave group to be output according to the output amplitude of the electrical-stimulation wave group calculated by the childbirth pain-relief station.

7. The bio-feedback type device for physical pain relief at childbirth of claim 1, wherein the electrical-stimulation wave group generator comprises a wave group sampled data memory, an automatic scanning circuit, D/A converter and an amplifying-driving circuit connected in sequence, wherein the wave group sampled data memory is configured to store the sampled data of at least two of the electrical-stimulation wave groups, the automatic scanning circuit is configured to generate address information with a digital logic circuit, and scan a waveform data storage unit a corresponding type at a sampling frequency of the electrical-stimulation wave group to cause the memory output wave group sampled data in turn, according to the output type of the electrical-stimulation wave group calculated by the childbirth pain-relief station; the D/A converter is configured to convert the wave group sampled data to an electrical-stimulation wave group, and the amplifying-driving circuit is configured to adjust the electrical-stimulation wave group to be output according to the output amplitude of the electrical-stimulation wave group calculated by the childbirth pain-relief station.

8. The bio-feedback type device for physical pain relief at childbirth of claim 1, further comprises an input and display module configured to interact with an operator or a device, and coupled to the childbirth pain-relief station.

* * * * *